United States Patent [19]

Cherry et al.

[11] Patent Number: 5,197,965
[45] Date of Patent: Mar. 30, 1993

[54] SKULL CLAMP PIN ASSEMBLY

[75] Inventors: Joseph A. Cherry, Mansfield; Victor B. Agbodoe, Boston; Raphael F. Meloul, Randolph; Jose E. Lizardi, Medfield, all of Mass.

[73] Assignee: Codman & Shurtleff, Inc., Randolph, Mass.

[21] Appl. No.: 921,866

[22] Filed: Jul. 29, 1992

[51] Int. Cl.5 .............................................. A61B 17/00
[52] U.S. Cl. ...................................... 606/54; 602/37; 5/637; 269/53
[58] Field of Search ................... 5/637, 622; 606/56, 606/96, 104; 269/53, 54, 54.1; 602/32, 37, 74, 17, 36, 39, 40, 59; 128/75

[56] References Cited

U.S. PATENT DOCUMENTS 2,966,383 12/1960 Boetcker, et al. .
3,099,441 7/1963 Ries .
4,169,478 10/1979 Hickmann .............................. 5/637
3,835,861 9/1974 Kees, et al. .
4,169,478 10/1979 Hickmann .
4,976,712 12/1990 Vanderslik ............................ 606/59

Primary Examiner—Richard J. Apley
Assistant Examiner—Beverly Meindl
Attorney, Agent, or Firm—Michael O. Tatlow

[57] ABSTRACT

A pin assembly for use in a skull clamp having a cylindrical non-metallic housing and a metallic rigid pin with a conical point fitted in the non-metallic housing. The non-metallic housing has fingers extending from a cavity in the surface of the housing and are positioned at an angle towards the pin end of the housing to hold the pin assembly in the skull clamp.

4 Claims, 2 Drawing Sheets

SKULL CLAMP PIN ASSEMBLY

FIELD OF INVENTION

This invention relates to a pin assembly to be used in a surgical head clamp or skull clamp to firmly hold the head of a patient in a position to allow a surgical procedure to be performed on the patients head. Head clamps or skull clamps are commonly used to hold the head of a patient in a fixed position during a neurosurgical procedure or other surgical procedure.

BACKGROUND OF THE INVENTION

It is important to rigidly hold the head of the patient in a fixed position during neurosurgical and related procedures. Patients heads are usually held in position with a head clamp which uses pads to hold the head or head clamps of the type shown in U.S. Pat. Nos. 2,966,383; 3,099,441; 3,835,861 and 4,169,478. These head clamps include a frame to hold at least three head engaging pin members that are forced through the skin of the patient to directly engage the bony portion of the skull. The engagement of the pins in the skull fixes the head in an immovable position during the surgical procedure. The pins that are used in these procedures are generally reusable and are fitted into pin sockets or bores in components affixed to the frame of the head clamp. The pins may be threaded into the bore or held in the bore with a pin or screw or held in the bore by an O-ring. After the pins have been used in a surgical procedure, they are cleaned and sterilized and packaged for subsequent use.

Occasionally, during a surgical procedure, it may be necessary to remove a patient's head from the skull clamp. In such instances it is sometimes desirable to replace the pins that are used in the skull clamp. Reusable, resterilized pins may not be readily available. The present invention provides pins which are disposable and can be marketed and maintained in a sterile condition in bacterial barrier packaging so that if such pins are needed in the operating room, they may be simply removed from the package and placed in the skull clamp. Since the pins are not reused, their points are sharp and easily placed in the bony portion of the skull of the patient.

SUMMARY OF THE PRESENT INVENTION

The skull pin assembly of the present invention comprises a metallic pin set in a non metallic housing. The pin housing is provided with flanges and fingers to secure the pin in the socket or bore of the skull clamp. Previously used disposable skull pins were simply placed in the pin socket or bore of the clamp and could fall out of the socket or bore if the head clamp was inverted or otherwise moved.

DETAIL DESCRIPTION OF THE INVENTION

Figure 1:
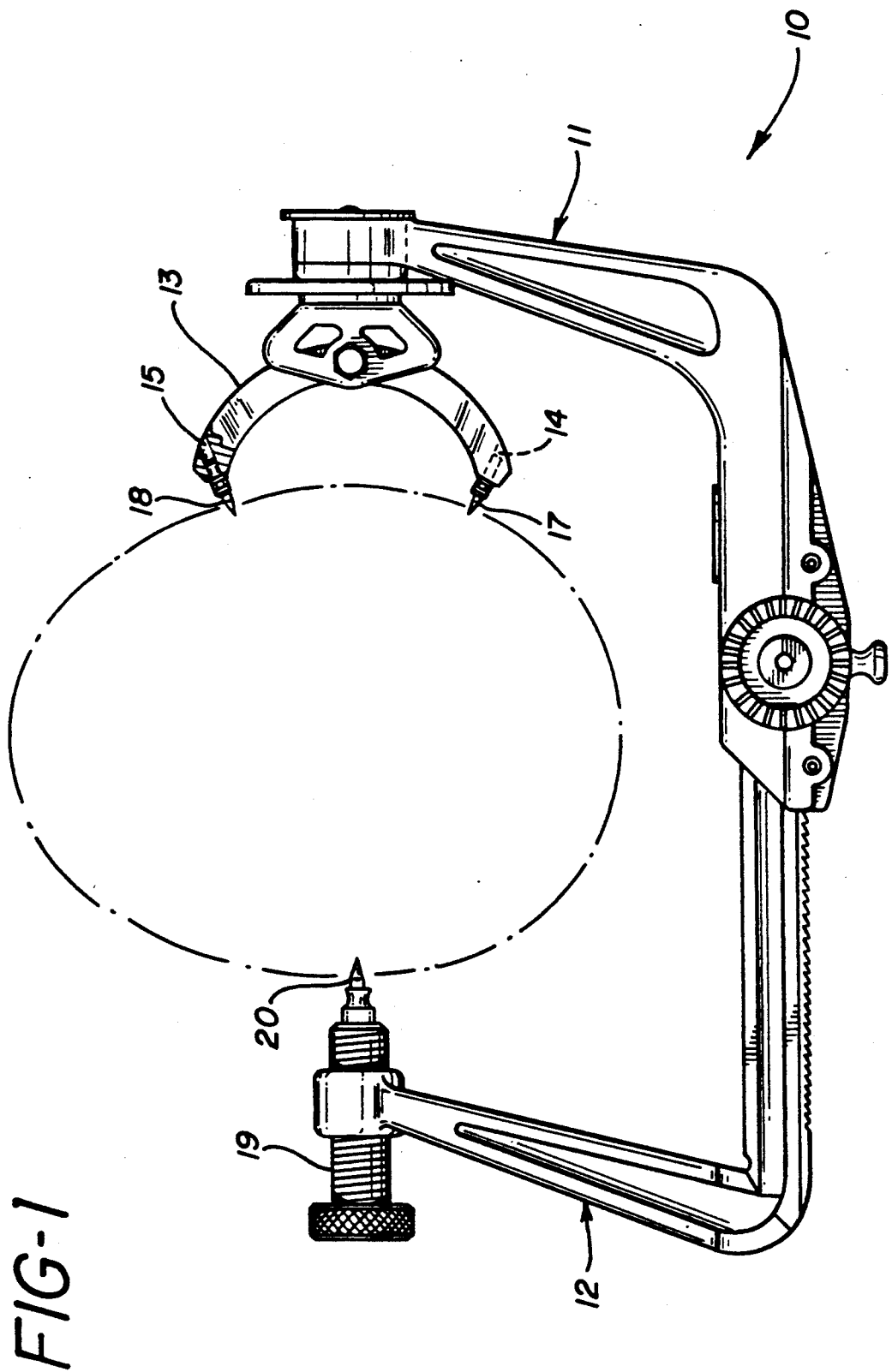
FIG. 1 shows a drawing of a typical head clamp, partially in cross section.
Figure 2:
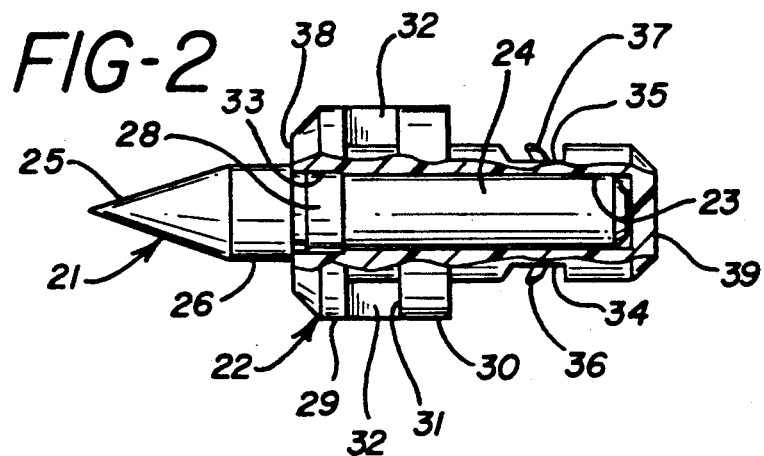
FIG. 2 shows a head clamp pin assembly of the present invention partially in cross section.
Figure 3:
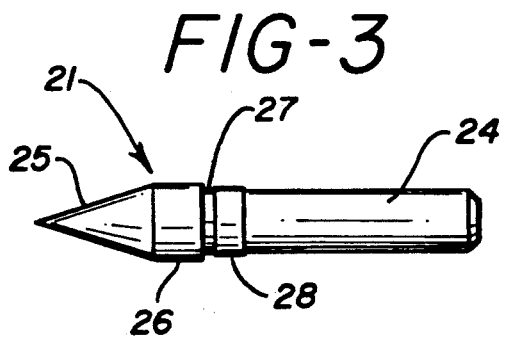
FIG. 3 shows the view of the metal portion of the pin assembly of the present invention.
Figure 4:
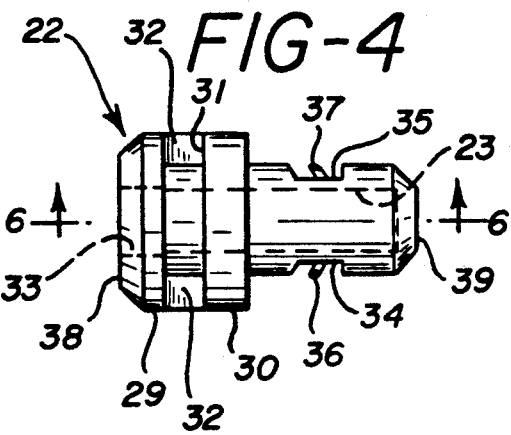
FIG. 4 shows a plan view of the non-metallic pin holder housing of the pin assembly of the present invention.
Figure 5:
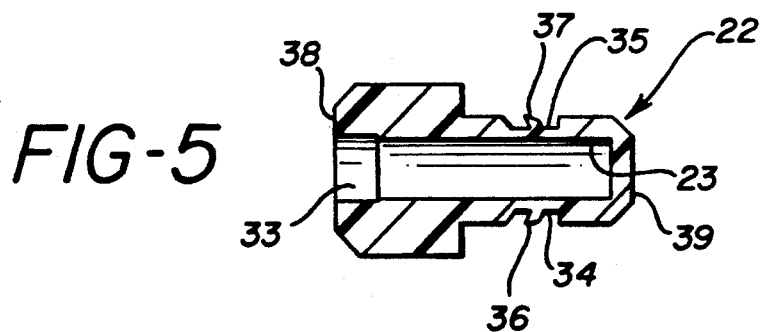
FIG. 5 is a cross sectional view of the non-metallic housing shown in FIG. 4.
Figure 6:
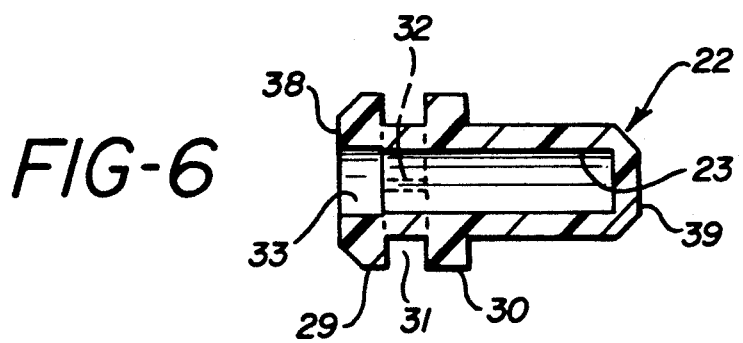
FIG. 6 is another cross sectional view of FIG. 4 taken along line 6—6 of FIG. 4.

The clamp of FIG. 1 is a typical design of surgical skull clamps. Particularly, the surgical head clamp shown in FIG. 1 is that device which is described in greater detail in U.S. Pat. No. 4,169,478, the disclosure of which is incorporated herein by reference. The clamp comprises a frame 10 having a fixed arm 11 and a rachet arm 2. The arms are capable of telescoping over each other to adjust the space between the arms. The fixed arm 11 has at its end a rocker arm 13 which have sockets 14 and 15 to receive and retain skull pins 17 and 18. At the end of rachet arm 12 there is a pin carrier 19 which has a pin 20 in a bore at one end. The pin carrier 19 is threaded for axial movement in a threaded boss at the end of rachet arm 12.

The pins 17, 18 and 20 are set in the patients skull in the following manner. The pin carrier 19 is placed in a position to allow maximum movement of the pin 20. The rachet arm 12 is moved toward the fixed arm until the skull pins are in contact with the patient's skull. The pins are positioned to enter the patient's scalp at a 90° angle, perpendicular to the surface of the head. The pin carrier 19 is then advanced toward the patient's skull until the pins 17, 18 and 20 are seated in the bony portion of the patient's skull.

The pin assembly of the present invention, comprises a non-metallic housing 22 and a rigid pin, member 21. The housing is made of a moldable plastic, preferably ABS (an acrylonitrile - butadiene styrene polymer) and the rigid pin member 21 is metal, preferably 17-4 PH stainless steel. There is a bore 23 in the non-metallic housing to receive the shank 24 of the pin member 21. The pin member 21 includes conical point 25 and a shoulder 26 immediately adjacent the conical point. There is a slight undercut 27 adjacent the shoulder whose purpose will be subsequently described. There is a step 28 adjacent the undercut which is slightly larger in diameter then the remainder of the shank of the pin.

The bore 23 of the non-metallic housing is substantially the same diameter as the diameter of the shank 24 of the pin. The bore 23 extends from a first end of the housing 38 into which the pin is inserted to a second end 39. The bore may be closed at the second end 39.

At the first end 38 of the pin around the opening of the bore there are two ribs 29 and 30 in the housing with a space 31 between the ribs. The purpose of the ribs is to allow forceps or other holding instruments to be introduced into the space 31 to place the housing of the pin into a socket 14, 15 or in the pin carrier 19 or to remove the pin assembly from a socket.

There are two axially extending ribs 32 between the circumferential ribs 29 and 30 to provide stability to the housing.

There is an enlarged diameter section 33 in the housing which has approximately the same diameter as the step 28 in the pin. This step is force fit into the enlarged diameter area 33 of the housing to securely hold the pin in the housing. The undercut 27 also assists in holding the metal pin in the housing. As the metal pin is forced into the housing, the plastic housing may deform and the material around the bore 23 then snaps into the uncut when the pin is fully seated.

On the body of the housing there are two cavities 34 and 35 cut through the transmerly surface of the body of the housing. In each of these cavities there is finger 36 and 37 which are set at an angle of between 30° and 60°, preferably 45° toward the opening of the bore. The fingers extend beyond the outer surface of the housing. These fingers assist in holding the pin in the socket of the clamp. The pin assembly should be held in the socket with a force of at least 5 pounds to ensure that the pin will not accidentally fall from the clamp if the clamp is rotated or inverted.

We claim:

1. A pin assembly for use in a skull clamp comprising;
    a cylindrical non-metallic housing having a first end and a second end and having an axially extending bore, said bore having an enlarged diameter at said first end, a plurality of spaced apart circumferential ribs surrounding the bore at said first end,
    a rigid pin having a conical point at a first end attached to a shank which extends to a second end of the pin, a shoulder portion between the conical point and the shank, an undercut in the shank adjacent the shoulder portion, a step in said shank having a diameter larger than the shank adapted to fit into the enlarged diameter of said bore,
    at least one transverse cavity in the outer surface of said non-metallic housing, a finger extending from the base of said cavity, said finger being positioned set in said cavity and extending at an angle toward said first end of said housing.

2. The pin assembly of claim 1 in which the rigid pin is metallic.

3. The pin assembly of claim 1 in which there are axially extending ribs between circumferential ribs around the bore at said first end of said housing.

4. The pin assembly of claim 1 in which said finger extends at an angle of between 30° and 60°.

* * * * *